(12) United States Patent
Von Teichert

(10) Patent No.: US 6,974,444 B2
(45) Date of Patent: Dec. 13, 2005

(54) SAFETY CATHETER

(76) Inventor: Joseph Von Teichert, 4125 S. Figueroa St., Unit 201, Los Angeles, CA (US) 90037

( * ) Notice: Subject to any disclaimer, the term of this patent is extended or adjusted under 35 U.S.C. 154(b) by 25 days.

(21) Appl. No.: 11/050,554

(22) Filed: Feb. 4, 2005

(65) Prior Publication Data
US 2005/0131348 A1 Jun. 16, 2005

Related U.S. Application Data

(62) Division of application No. 09/932,797, filed on Aug. 20, 2001, now Pat. No. 6,860,872.

(51) Int. Cl.⁷ .............................................. A61M 5/178
(52) U.S. Cl. .................. 604/164.08; 604/263; 128/919
(58) Field of Search ...................... 604/164.01, 164.07, 604/164.08, 165.01, 165.02, 165.03, 167.01–167.04, 604/177, 192, 196, 198; 128/919

(56) References Cited

U.S. PATENT DOCUMENTS

| | | | | |
|---|---|---|---|---|
| 4,627,843 A | * | 12/1986 | Raines | 604/263 |
| 4,631,058 A | * | 12/1986 | Raines | 604/263 |
| 4,676,783 A | * | 6/1987 | Jagger et al. | 604/171 |
| 4,693,708 A | * | 9/1987 | Wanderer et al. | 604/198 |
| 4,820,282 A | | 4/1989 | Hogan | |
| 4,941,881 A | * | 7/1990 | Masters et al. | 604/162 |
| 5,067,945 A | | 11/1991 | Ryan et al. | |
| 5,120,320 A | * | 6/1992 | Fayngold | 604/177 |
| 5,169,391 A | * | 12/1992 | Vogel | 604/177 |
| 5,195,974 A | * | 3/1993 | Hardy | 604/110 |
| 5,219,339 A | * | 6/1993 | Saito | 604/198 |
| 5,342,309 A | | 8/1994 | Hausser | |
| 5,385,555 A | | 1/1995 | Hausser | |
| 5,647,849 A | | 7/1997 | Kalin | |
| 5,658,254 A | | 8/1997 | Reichenbach et al. | |
| 5,697,908 A | | 12/1997 | Imbert et al. | |
| 5,733,264 A | | 3/1998 | Flowers | |
| 5,743,887 A | | 4/1998 | Brattesani | |
| 5,851,196 A | | 12/1998 | Arnett | |
| 5,882,342 A | | 3/1999 | Cooper et al. | |
| 5,885,256 A | * | 3/1999 | Chern et al. | 604/192 |
| 5,931,815 A | | 8/1999 | Liu | |
| 5,938,641 A | | 8/1999 | Villanueva | |
| 6,860,872 B2 | * | 3/2005 | Teichert | 604/198 |

\* cited by examiner

Primary Examiner—LoAn H. Thanh
(74) Attorney, Agent, or Firm—David A. Belasco; Belasco Jacobs & Townsley, LLP

(57) ABSTRACT

The invention pertains to safety syringes and safety catheters designed to protect the operator from unintentional needle sticks and prevent fluid leakage after use. When the safety catheter is in operation, fluid passes from the flexible tubing through the hollow body, outlet portion, and out of the hollow needle. The hollow body includes a pair of wings to attach to the patient's skin. A needle shield fits slidably over the needle and a portion of the hollow body and includes a slot accommodating the attachable wings. The needle shield is a membrane sealed body. The shield includes an internal membrane sealing against fluid loss through the wing slots. The needle shield's first position permits the needle's tip to extend outward from the shield through a membrane. When in the second position, the needle shield extends beyond the needle's tip preventing any fluid loss.

5 Claims, 3 Drawing Sheets

SAFETY CATHETER

RELATED APPLICATION

The instant application is a divisional application of U.S. patent application Ser. No. 09/932,797, filed Aug. 20, 2001 now U.S. Pat. No. 6,860,872.

FIELD OF INVENTION

The invention pertains to medical devices and more particularly to syringes and catheters designed to protect patients and health care workers from unintentional needle sticks and to prevent leakage of fluid from the device after use.

BACKGROUND OF THE INVENTION

In the wake of the HIV epidemic, new and more virulent strains of hepatitis and other blood related diseases, health care workers have become increasingly aware of the potential for deadly consequences related to accidental or unintentional needle sticks or other contact with contaminated bodily fluids. As catheters and syringes are used in immense numbers in modern hospitals and other health care facilities, the opportunity for injury and resulting contamination is significant.

Various devices have been invented in an effort to prevent such injuries. U.S. Pat. No. 5,733,264 issued to Flowers in 1998 discloses a syringe equipped with a sliding tubular shield that slides over the exposed needle after use and locks in place. This shield is, however, open on the distal end, thus permitting fluids to leak from the needle and out the end of the shield. U.S. Pat. No. 5,342,309 issued to Hausser in 1994 is similar in design to the Flowers invention, however employing different means for locking the safety shield in the distal position. Like Flowers, it would appear to be nearly impossible to position this shield over the needle with one hand.

U.S. Pat. No. 5,743,887 issued to Brattesani in 1998 provides for a docking base to help protect the health care worker while attaching and removing the needle from the syringe device. This invention fails to provide a means to control leaks from the needle even though it is encased in a movable safety shield. Likewise, the movement of this shield cannot be easily controlled with one hand. U.S. Pat. No. 5,385,555 issued to Hausser in 1995 is directed towards a syringe having a lockable safety shield slidably positionable over the needle after use. This device also requires two hands to operate and makes no provision for containing any fluid that may drip from the needle.

U.S. Pat. No. 5,647,849 issued to Kalin in 1997 discloses a safety syringe having a slidable barrel that can be positioned over the needle to prevent unwanted injuries. The syringe is provided with a removable seal at the end of the barrel. However, once this seal is removed, there is no convenient way of reattaching the seal to the barrel and thus the potential for leakage remains. Of a slightly different nature, U.S. Pat. No. 4,820,282 issued to Hogan in 1987 relates to a sheath for use in removing hypodermic needles from patients and retaining the point of the removed needle in the sheath when the needle and sheath are disposed of so as to protect against accidentally being pricked.

It is an objective of the invention to provide a means to effectively shield the needle of a syringe or catheter after the device is removed from a patient, thereby preventing accidental needle sticks. It is a further objective of the invention to prevent leakage of fluids from the needle of the catheter or syringe after use. It is yet a further objective of the invention that the shielding capability can be operated with the hand that is operating the syringe or removing the catheter. It is still a further objective of the invention that the safety shield is simple and inexpensive to manufacture.

SUMMARY OF THE INVENTION (1) A safety infusion set may be constructed from the following components. A length of flexible tubing having a first end and a second end is provided. A hollow catheter body is provided. The body has a first end, a second end, an outer surface and an outlet portion, and is fixedly attached at its first end to the first end of the tubing. A pair of attachment wings is provided. The attachment wings are fixedly attached to the outer surface of the catheter body. The outlet portion has a first end, a center section and a second end and is fixedly attached at its first end to the second end of the catheter body. A connection fitting attached to the second end of the tubing. A hollow needle is provided. The needle has a first end and a second end and is fixedly attached at its first end to the second end of the outlet portion such that fluid may pass from the flexible tubing, through the catheter body and the outlet portion and outwardly through the hollow needle.

A needle shield is provided. The shield has an outer surface, a first end, a second end, and is sized and shaped to fit slidably over the needle, outlet portion, and at least a portion of the catheter body. The needle shield has a cylindrical portion beginning at the second end of the shield. The cylindrical portion has an outer end and an inner end and is sized and shaped to fit over the outlet portion, and a slotted portion. The slotted portion has a longitudinal slot, extending from the inner end of the cylindrical portion toward the first end of the shield. The slotted portion is sized and shaped to fit slidably over the hollow catheter body with the slot accommodating an intersection of the wings and the catheter body.

Means are provided for securing the needle shield at its first end to the catheter body in a first position. The first position permits the second end of the needle to extend outwardly from the second end of the shield. A second position permits the second end of the needle shield to extend beyond the second end of the needle. Means are provided for moving the needle shield from the first position to the second position using a single hand. Means are provided for containing any fluid leaking from the second end of the needle within the needle shield when the shield is secured to the catheter body in the second position.

(2) In a variant of the invention, the means for securing the needle shield at its first end to the catheter body in first and second positions includes a first surrounding groove. The first groove is located on the outer surface of the catheter body adjacent its second end. A second surrounding groove is provided. The second groove is located on the outer surface of the catheter body adjacent its first end. An engaging finger is provided. The finger is formed of resilient material and has an upper surface, a lower surface, an activating end, an attaching end and a pivot point located between the ends. A securing tooth is provided. The tooth has an upper end and a lower end and is fixedly attached at its upper end to the lower surface of the engaging finger adjacent the attaching end.

The securing tooth is sized, shaped and located to removably engage one of the first and second surrounding grooves on the catheter body. A mounting post is provided. The post has an upper end, a lower end and is fixedly mounted at its lower end to the outer surface of the needle shield adjacent its first end. The post is fixedly attached at its upper end to the lower surface of the engaging finger at the pivot point such that the resilient material of the engagement finger will bias the securing tooth downwardly to removably engage one of the first and second surrounding grooves.

When pressure is applied to the upper surface of the engaging finger adjacent its activating end the securing tooth will pivot upwardly away from one of the first and second securing grooves, permitting the needle shield to move slidably from the first position to the second position. When the securing tooth is positioned over one of the first and second securing grooves and pressure is relieved from the upper surface of the engaging finger the securing tooth will engage one of the grooves, preventing further movement of the needle shield.

(3) In a further variant, the means for moving the needle shield from the first position to the second position using a single hand further includes an indentation. The indentation is located upon the outer surface of the needle shield adjacent it's first end and is sized and shaped to engage a finger pad of a user.

(4) In yet another variant of the invention, the means for containing any fluid leaking from the second end of the needle within the needle shield when the shield is secured to the catheter body in the second position includes a first sealing membrane. The membrane is fixedly attached to the outer end of the cylindrical portion of the needle shield and permits the hollow needle and the second end and center section of the outlet portion to pass through the membrane when the needle shield is in the first position. A second sealing membrane is provided. The second membrane is fixedly attached to the inner end of the cylindrical portion of the needle shield and permits the hollow needle and the second end and center section of the outlet portion to pass through the membrane when the needle shield is in the first position. The first sealing membrane is capable of sealing the outer end of the cylindrical portion of the needle shield when the shield is in the second position with the hollow needle positioned within the cylindrical portion. The second sealing membrane is capable of sealing the inner end of the cylindrical portion of the needle shield about the needle when the shield is in the second position with the outlet portion positioned within the slotted portion of the shield.

(5) In a final variant, the means for containing any fluid leaking from the second end of the needle within the needle shield when the shield is secured to the catheter body in the second position includes a first sealing membrane. The first membrane is fixedly attached to the outer end of the cylindrical portion of the needle shield and permits the hollow needle to pass through the membrane when the needle shield is in the first position. A second sealing membrane is provided. The second membrane is fixedly attached to the inner end of the cylindrical portion of the needle shield and permits the hollow needle to pass through the membrane when the needle shield is in the first position. The first sealing membrane being capable of sealing the outer end of the cylindrical portion of the needle shield when the shield is in the second position with the hollow needle positioned within the cylindrical portion. The second sealing membrane is capable of sealing the inner end of the cylindrical portion of the needle shield about the needle when the shield is in the second position with the outlet portion positioned within the slotted portion of the shield.

Figure 1:
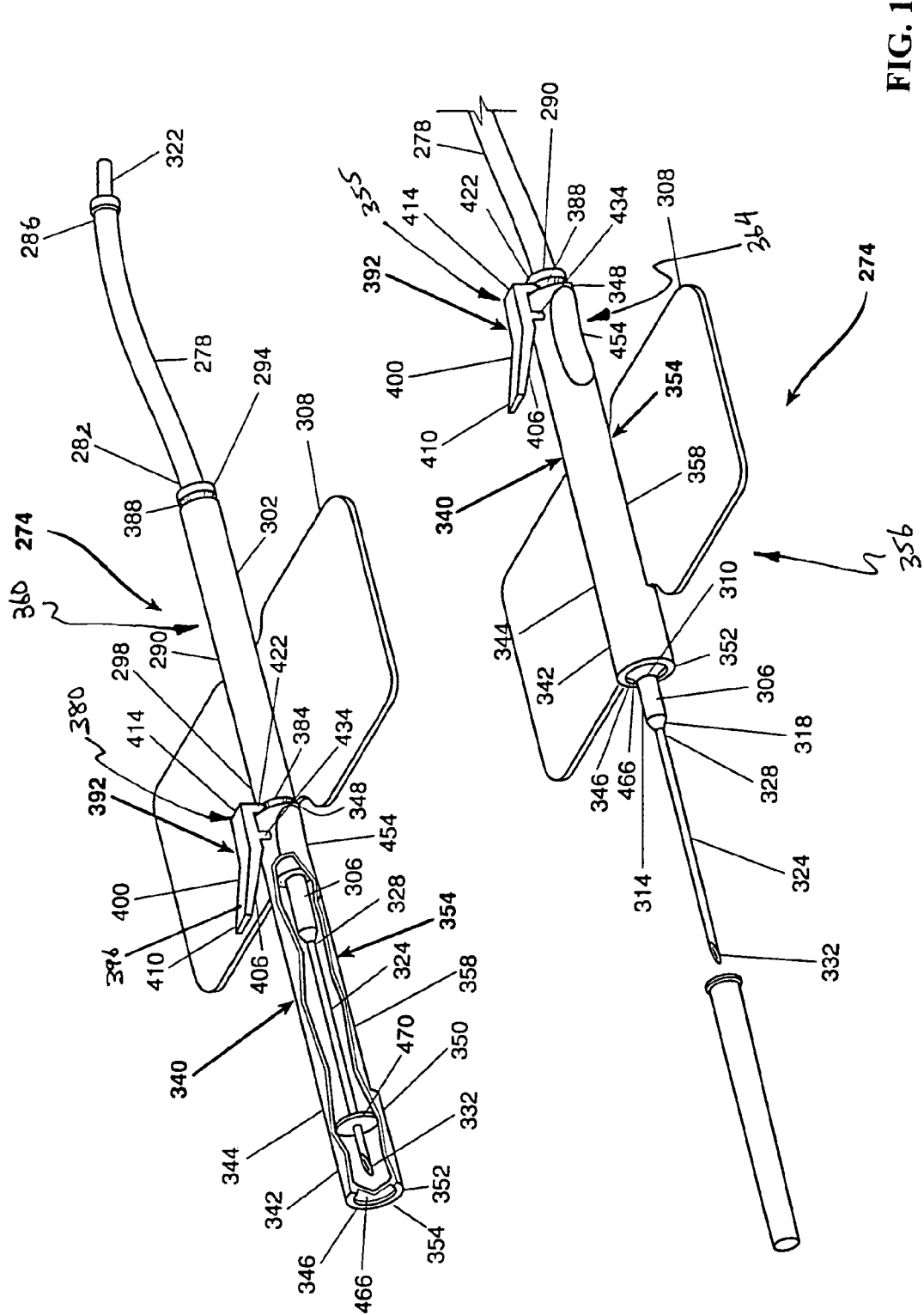
FIG. 1 is a perspective view of a first embodiment of the safety infusion set illustrating the needle shield in a first, closed position and in a second, open position with the outlet portion of the needle extending through the sealing membranes.

DETAILED DESCRIPTION OF THE PREFERRED EMBODIMENT (1) As shown in FIG. 1, a safety infusion set 274 includes a length of flexible tubing 278 having a first end 282 and a second end 286. A hollow catheter body 290 is provided. The body 290 has a first end 294, a second end 298, an outer surface 302 and an outlet portion 306, and is fixedly attached at its first end 294 to the first end 282 of the tubing 278. A pair of attachment wings 308 is provided. The attachment wings 308 are fixedly attached to the outer surface 302 of the catheter body 290. The outlet portion 306 has a first end 310, a center section 314 and a second end 318 and is fixedly attached at its first end 310 to the second end 298 of the catheter body 290. A connection fitting 322 attached to the second end 286 of the tubing 278. A hollow needle 324 is provided. The needle 324 has a first end 328 and a second end 332 and is fixedly attached at its first end 328 to the second end 318 of the outlet portion 306 such that fluid 336 may pass from the flexible tubing 278, through the catheter body 290 and the outlet portion 306 and outwardly through the hollow needle 324.

A needle shield 340 is provided. The shield 340 has an outer surface 344, a first end 348, a second end 352, and is sized and shaped to fit slidably over the needle 324, outlet portion 306, and at least a portion of the catheter body 290. The needle shield 340 has a cylindrical portion 342 beginning at the second end 352 of the shield 340. The cylindrical portion 342 has an outer end 346 and an inner end 350 and is sized and shaped to fit over the outlet portion 306, and a slotted portion 354. The slotted portion 354 has a longitudinal slot 358, extending from the inner end 350 of the cylindrical portion 342 toward the first end 348 of the shield 340. The slotted portion 354 is sized and shaped to fit slidably over the hollow catheter body 290 with the slot 354 accommodating an intersection of the wings 308 and the catheter body 290.

Means 355 are provided for securing the needle shield 340 at its first end 348 to the catheter body 290 in a first position 356. The first position 356 permits the second end 332 of the needle 324 to extend outwardly from the second end 352 of the shield 340. A second position 360 permits the second end 352 of the needle shield 340 to extend beyond the second end 332 of the needle 324. Means 364 are provided for moving the needle shield 340 from the first position 356 to the second position 360 using a single hand 368 (not shown). Means 372 are provided for containing any fluid leaking 376 from the second end 332 of the needle 324 within the needle shield 340 when the shield 340 is secured to the catheter body 290 in the second position 360.

Figure 2:
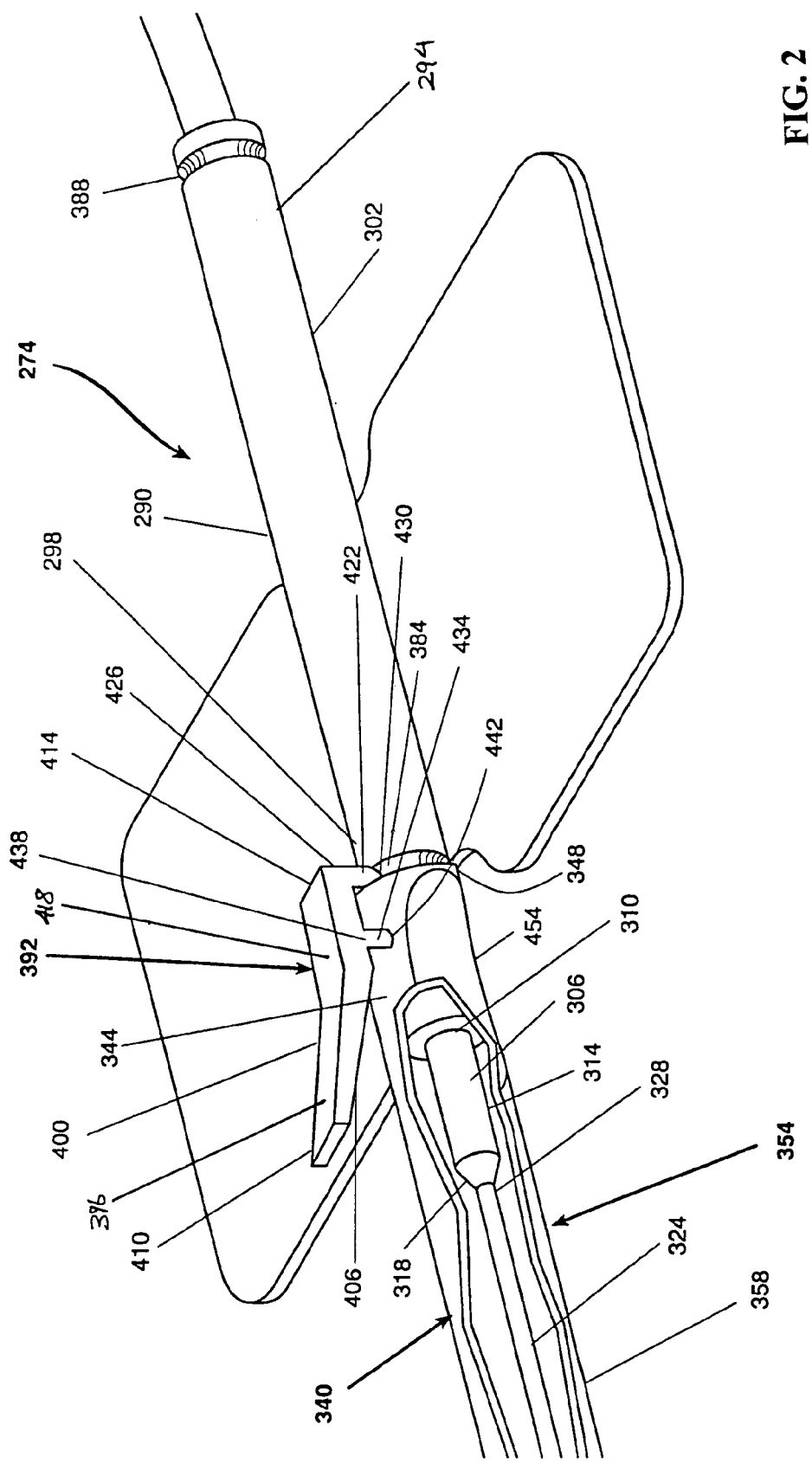
FIG. 2 is a detailed perspective view of the FIG. 1 embodiment illustrating the means for securing the needle shield.

(2) In another variant, as shown in FIG. 2, the means 380 for securing the needle shield 340 at its first end 348 to the catheter body 290 in first 356 and second positions 360 includes a first surrounding groove 384. The first groove 384 is located on the outer surface 302 of the catheter body 290 adjacent its second end 298. A second surrounding groove 388 is provided. The second groove 388 is located on the outer surface 302 of the catheter body 290 adjacent its first end 294. An engaging finger 392 is provided. The finger 392 is formed of resilient material 396 and has an upper surface 400, a lower surface 406, an activating end 410, an attaching end 414 and a pivot point 418 located between the ends. A securing tooth 422 is provided. The tooth 422 has an upper end 426 and a lower end 430 and is fixedly attached at its upper end 426 to the lower surface 406 of the engaging finger 392 adjacent the attaching end 414.

The securing tooth 422 is sized, shaped and located to removably engage one of the first 384 and second surrounding grooves 388 on the catheter body 290. A mounting post 434 is provided. The post 434 has an upper end 438, a lower end 442 and is fixedly mounted at its lower end 442 to the outer surface 344 of the needle shield 340 adjacent its first end 348. The post 434 is fixedly attached at its upper end 438 to the lower surface 406 of the engaging finger 392 at the pivot point 418 such that the resilient material 396 of the engagement finger 392 will bias the securing tooth 422 downwardly to removably engage one of the first 384 and second surrounding grooves 388.

When pressure is applied to the upper surface 400 of the engaging finger 392 adjacent its activating end 410 the securing tooth 422 will pivot upwardly away from one of the first 384 and second securing grooves 388, permitting the needle shield 340 to move slidably from the first position 356 to the second position 360. When the securing tooth 422 is positioned over one of the first 384 and second securing grooves 388 and pressure is relieved from the upper surface 400 of the engaging finger 392 the securing tooth 422 will engage one of the grooves, preventing further movement of the needle shield 340.

Figure 3:
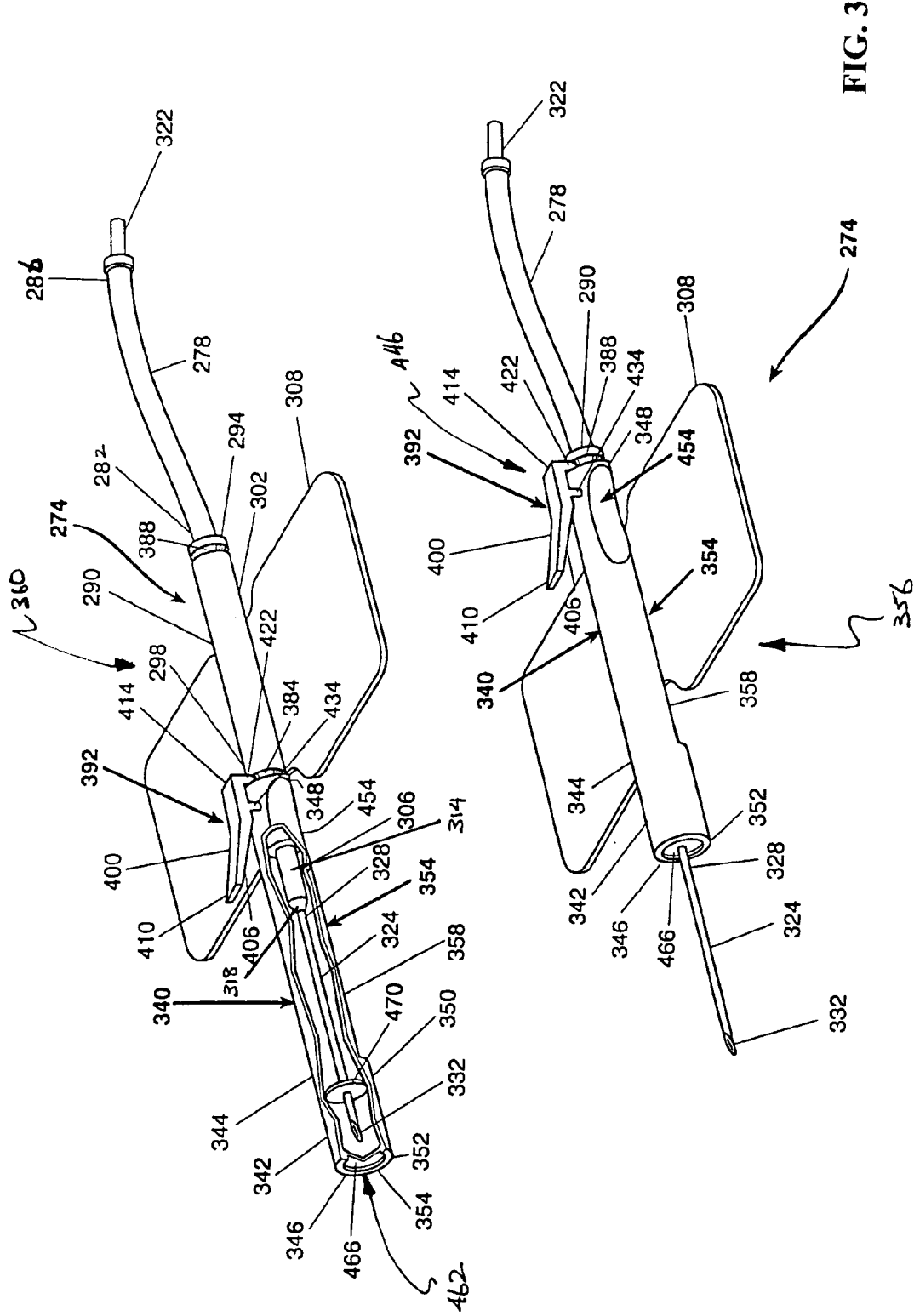
FIG. 3 is a perspective view of a second embodiment of the safety infusion set illustrating the needle shield in a first, closed position and in a second, open position with the needle alone extending through the sealing membranes.

(3) In a further variant, as shown in FIG. 3, the means 446 for moving the needle shield 340 from the first position 356 to the second position 360 using a single hand 450 (not shown) further includes an indentation 454. The indentation 454 is located upon the outer surface 344 of the needle shield 340 adjacent its first end 348 and is sized and shaped to engage a finger pad 458 (not shown) of a user.

(4) In another variant of the invention, as shown in FIG. 1, the means 462 for containing any fluid leaking 376 from the second end 332 of the needle 324 within the needle shield 340 when the shield 340 is secured to the catheter body 290 in the second position 360 includes a first sealing membrane 466. The membrane 466 is fixedly attached to the outer end 346 of the cylindrical portion 342 of the needle shield 340 and permits the hollow needle 324 and the second end 318 and center section 314 of the outlet portion 306 to pass through the membrane 466 when the needle shield 340 is in the first position 356. A second sealing membrane 470 is provided. The second membrane 470 is fixedly attached to the inner end 350 of the cylindrical portion 342 of the needle shield 340 and permits the hollow needle 324 and the second end 318 and center section 314 of the outlet portion 306 to pass through the membrane 470 when the needle shield 340 is in the first position 356.

The first sealing membrane 466 is capable of sealing the outer end 346 of the cylindrical portion 342 of the needle shield 340 when the shield 340 is in the second position 360 with the hollow needle 324 positioned within the cylindrical portion 342. The second sealing membrane 470 is capable of sealing the inner end 350 of the cylindrical portion 342 of the needle shield 340 about the needle 324 when the shield 340 is in the second position 360 with the outlet portion 306 positioned within the slotted portion 354 of the shield 340.

(5) In a final variant, as shown in FIG. 3, the means 472 for containing any fluid leaking 376 from the second end 332 of the needle 324 within the needle shield 340 when the shield 340 is secured to the catheter body 290 in the second position 360 includes a first sealing membrane 466. The first membrane 466 is fixedly attached to the outer end 346 of the cylindrical portion 342 of the needle shield 340 and permits the hollow needle 324 to pass through the membrane 466 when the needle shield 340 is in the first position 356. A second sealing membrane 470 is provided. The second membrane 470 is fixedly attached to the inner end 350 of the cylindrical portion 342 of the needle shield 340 and permits the hollow needle 324 to pass through the membrane 470 when the needle shield 340 is in the first position 356. The first sealing membrane 466 is capable of sealing the outer end 346 of the cylindrical portion 342 of the needle shield 340 when the shield 340 is in the second position 360 with the hollow needle 324 positioned within the cylindrical portion 342. The second sealing membrane 470 is capable of sealing the inner end 350 of the cylindrical portion 342 of the needle shield 340 about the needle 324 when the shield 340 is in the second position 360 with the outlet portion 306 positioned within the slotted portion 354 of the shield 340.

The safety syringe/catheter 10 has been described with reference to particular embodiments. Other modifications and enhancements can be made without departing from the spirit and scope of the claims that follow.

What is claimed is:

1. A safety infusion set, comprising:
   a length of flexible tubing, said tubing having a first end and a second end;
   a hollow catheter body, said body having a first end, a second end, an outer surface and an extended outlet portion, and being fixedly attached at its first end to the first end of the tubing;
   a pair of attachment wings, said attachment wings being fixedly attached to the outer surface of the catheter body;
   said outlet portion having a first end, a center section and a second end and being fixedly attached at its first end to the second end of the catheter body;
   a connection fitting attached to the second end of the tubing;
   a hollow needle, said needle having a first end and a second end and being fixedly attached at its first end to the second end of the outlet portion such that fluid may pass from the flexible tubing, through the catheter body and the outlet portion and outwardly through the hollow needle;
   a needle shield, said shield having an outer surface, a first end, a second end, and being sized and shaped to fit slidably over the needle, the outlet portion and at least a portion of the catheter body;
   said needle shield having a cylindrical portion commencing at the second end of the shield, said cylindrical portion having an outer end and an inner end and being sized and shaped to fit over the outlet portion, and a slotted portion, said slotted portion having a longitudinal slot, extending from the inner end of the cylindrical portion toward the first end of the shield, said slotted portion being sized and shaped to fit slidably over the hollow catheter body with said slot accommodating an intersection of the wings and the catheter body;

means for securing the needle shield at its first end to the catheter body in a first position, said first position permitting the second end of the needle to extend outwardly from the second end of the shield and in a second position in which the second end of the needle shield extends beyond the second end of the needle;

means for moving the needle shield from the first position to the second position using a single hand; and means for containing any fluid leaking from the second end of the needle within the needle shield when the shield is secured to the catheter body in the second position.

2. A safety infusion set as described in claim 1, wherein the means for securing the needle shield at its first end to the catheter body in first and second positions further comprises:

a first surrounding groove, said first groove disposed upon the outer surface of the catheter body adjacent its second end;

a second surrounding groove, said second groove disposed upon the outer surface of the catheter body adjacent its first end;

an engaging finger, said finger being formed of resilient material and having an upper surface, a lower surface, an activating end, an attaching end and a pivot point disposed between said ends;

a securing tooth, said tooth having an upper end and a lower end and being fixedly attached at its upper end to the lower surface of the engaging finger adjacent the attaching end;

said securing tooth being sized, shaped and disposed to removably engage one of the first and second surrounding grooves on the catheter body;

a mounting post, said post having an upper end, a lower end and being fixedly mounted at its lower end to the outer surface of the needle shield adjacent its first end;

said post being fixedly attached at its upper end to the lower surface of the engaging finger at the pivot point such that the resilient material of the engagement finger will bias the securing tooth downwardly to removably engage one of the first and second surrounding grooves; and whereby, when pressure is applied to the upper surface of the engaging finger adjacent its activating end the securing tooth will pivot upwardly away from one of the first and second securing grooves, thereby permitting the needle shield to move slidably from the first position to the second position and when the securing tooth is positioned over one of the first and second securing grooves and pressure is relieved from the upper surface of the engaging finger the securing tooth will engage one of said grooves, thereby preventing further movement of the needle shield.

3. A safety infusion set as described in claim 1, wherein the means for moving the needle shield from the first position to the second position using a single hand further comprises an indentation, said indentation being disposed upon the outer surface of the needle shield adjacent its first end and being sized and shaped to engage a finger pad of a user.

4. A safety infusion set as described in claim 1, wherein the means for containing any fluid leaking from the second end of the needle within the needle shield when the shield is secured to the catheter body in the second position further comprises:

a first sealing membrane, said first membrane being fixedly attached to the outer end of the cylindrical portion of the needle shield and permitting the hollow needle and the second end and center section of the outlet portion to pass through the membrane when the needle shield is in the first position;

a second sealing membrane, said second membrane being fixedly attached to the inner end of the cylindrical portion of the needle shield and permitting the hollow needle and the second end and center section of the outlet portion to pass through the membrane when the needle shield is in the first position;

said first sealing membrane being capable of sealing the outer end of the cylindrical portion of the needle shield when the shield is in the second position with the hollow needle positioned within the cylindrical portion; and said second sealing membrane being capable of sealing the inner end of the cylindrical portion of the needle shield about the needle when the shield is in the second position with the outlet portion positioned within the slotted portion of the shield.

5. A safety infusion set as described in claim 1, wherein the means for containing any fluid leaking from the second end of the needle within the needle shield when the shield is secured to the catheter body in the second position further comprises:

a first sealing membrane, said first membrane being fixedly attached to the outer end of the cylindrical portion of the needle shield and permitting the hollow needle to pass through the membrane when the needle shield is in the first position;

a second sealing membrane, said second membrane being fixedly attached to the inner end of the cylindrical portion of the needle shield and permitting the hollow needle to pass through the membrane when the needle shield is in the first position;

said first sealing membrane being capable of sealing the outer end of the cylindrical portion of the needle shield when the shield is in the second position with the hollow needle positioned within the cylindrical portion; and said second sealing membrane being capable of sealing the inner end of the cylindrical portion of the needle shield about the needle when the shield is in the second position with the outlet portion positioned within the slotted portion of the shield.

* * * * *